(12) United States Patent
Yang et al.

(10) Patent No.: US 8,337,764 B2
(45) Date of Patent: Dec. 25, 2012

(54) RECESS WAVEGUIDE MICROWAVE CHEMICAL PLANT FOR PRODUCTION OF ETHENE FROM NATURAL GAS AND THE PROCESS USING SAID PLANT

(76) Inventors: Hongsheng Yang, Jiangsu (CN); Dekun Sun, Jiangsu (CN)

( * ) Notice: Subject to any disclaimer, the term of this patent is extended or adjusted under 35 U.S.C. 154(b) by 829 days.

(21) Appl. No.: 12/085,800

(22) PCT Filed: Nov. 10, 2006

(86) PCT No.: PCT/CN2006/003015
§ 371 (c)(1), (2), (4) Date: Oct. 28, 2008

(87) PCT Pub. No.: WO2007/082438
PCT Pub. Date: Jul. 26, 2007

(65) Prior Publication Data
US 2009/0218211 A1    Sep. 3, 2009

(30) Foreign Application Priority Data
Jan. 20, 2006  (CN) .......................... 2006 1 0037890

(51) Int. Cl.
*B01J 19/12* (2006.01)
*H01P 1/207* (2006.01)
*H01P 5/107* (2006.01)
*H01P 3/08* (2006.01)
*H01P 7/06* (2006.01)

(52) U.S. Cl. .................. 422/186; 422/186.29; 333/157; 333/227; 333/232; 333/233

(58) Field of Classification Search ............. 204/157.43, 204/158.21, 165; 422/21, 82.11, 186, 186.29; 333/227, 230, 232, 248, 21 R, 157, 233; 118/723 MW; 219/678, 690
See application file for complete search history.

(56) References Cited

U.S. PATENT DOCUMENTS

| | | | | | |
|---|---|---|---|---|---|
| 2,428,287 | A | * | 9/1947 | Linder | 333/233 |
| 2,530,836 | A | * | 11/1950 | Mumford | 332/165 |
| 2,702,886 | A | * | 2/1955 | Collard | 333/254 |
| 2,703,365 | A | * | 3/1955 | Ginzton et al. | 333/232 |
| 2,749,477 | A | * | 6/1956 | Verweel | 315/39 |

(Continued)

FOREIGN PATENT DOCUMENTS
CN    2108997 U    7/1992
(Continued)

OTHER PUBLICATIONS

Machine translation of CN 1588690.*

(Continued)

*Primary Examiner* — Keith Hendricks
*Assistant Examiner* — Colleen M Raphael
(74) *Attorney, Agent, or Firm* — Christie, Parker & Hale, LLP (57) ABSTRACT

A recess waveguide microwave chemical plant for production of ethene from natural gas and a process for production of ethene using the plant. The plant includes a recess waveguide, a mode transducer and coupling orifice plate, an adjustable short-circuiting plunger, and a chemical reactor; wherein with the recess waveguide as a main body, the mode transducer and coupling orifice plate is at the left side of the recess waveguide, the adjustable short-circuiting plunger is at the right side of the recess waveguide, and the chemical reactor is across the recess waveguide.

11 Claims, 6 Drawing Sheets

U.S. PATENT DOCUMENTS

| | | | | |
|---|---|---|---|---|
| 2,807,745 | A * | 9/1957 | Moll | 315/5.22 |
| 2,998,579 | A * | 8/1961 | Rizzi | 332/163 |
| 3,042,882 | A * | 7/1962 | Jamison et al. | 333/102 |
| 3,221,204 | A * | 11/1965 | Scott et al. | 315/3.5 |
| 3,315,187 | A * | 4/1967 | Nakahara et al. | 333/239 |
| 3,806,842 | A * | 4/1974 | Slevin et al. | 333/227 |
| 3,918,064 | A * | 11/1975 | Gustincic | 343/783 |
| 4,099,145 | A * | 7/1978 | Boujet | 333/21 R |
| 4,553,266 | A * | 11/1985 | Bates et al. | 455/327 |
| 4,576,692 | A * | 3/1986 | Fukuta et al. | 422/186 |
| 4,673,897 | A * | 6/1987 | Chua et al. | 333/26 |
| 4,745,337 | A * | 5/1988 | Pichot et al. | 204/298.37 |
| 4,883,570 | A * | 11/1989 | Efthimion et al. | 204/193 |
| 5,008,506 | A * | 4/1991 | Asmussen et al. | 219/696 |
| 5,049,843 | A * | 9/1991 | Barnes et al. | 333/246 |
| 5,205,912 | A | 4/1993 | Murphy | |
| 5,230,784 | A * | 7/1993 | Yoshida | 204/298.19 |
| 5,300,901 | A * | 4/1994 | Krummel et al. | 333/99 PL |
| 5,340,450 | A * | 8/1994 | Griffiths et al. | 204/157.43 |
| 5,343,176 | A * | 8/1994 | Hasler | 333/204 |
| 5,393,492 | A * | 2/1995 | Di Martino et al. | 422/62 |
| 5,470,541 | A * | 11/1995 | Koch et al. | 204/157.43 |
| 5,606,723 | A * | 2/1997 | Morse et al. | 422/186.29 |
| 5,782,897 | A * | 7/1998 | Carr | 607/101 |
| 5,834,744 | A * | 11/1998 | Risman | 219/697 |
| 5,869,817 | A * | 2/1999 | Zietlow et al. | 219/696 |
| 5,965,786 | A * | 10/1999 | Rostaing et al. | 204/157.3 |
| 5,993,612 | A * | 11/1999 | Rostaing et al. | 204/157.3 |
| 6,011,453 | A * | 1/2000 | Glinder et al. | 333/248 |
| 6,160,031 | A * | 12/2000 | Poree et al. | 204/157.43 |
| 6,190,510 | B1 * | 2/2001 | Rostaing et al. | 204/164 |
| 6,224,836 | B1 * | 5/2001 | Moisan et al. | 422/186 |
| 6,592,723 | B2 * | 7/2003 | Cha | 204/157.47 |
| 6,700,548 | B1 * | 3/2004 | Chen et al. | 343/771 |
| 6,783,632 | B2 * | 8/2004 | Cha | 204/157.47 |
| 6,847,270 | B2 * | 1/2005 | Yoneda et al. | 333/135 |
| 6,870,123 | B2 * | 3/2005 | Suzuki et al. | 219/121.43 |
| 6,960,747 | B2 * | 11/2005 | Risman | 333/225 |
| 7,408,427 | B1 * | 8/2008 | Lee-Yow et al. | 333/126 |
| 2003/0159781 | A1 * | 8/2003 | Van Stralen et al. | 118/723 MW |
| 2006/0021980 | A1 * | 2/2006 | Lee et al. | 422/186 |
| 2009/0045891 | A1 * | 2/2009 | Okamoto et al. | 333/239 |

FOREIGN PATENT DOCUMENTS

| | | |
|---|---|---|
| CN | 2125878 U | 12/1992 |
| CN | 1250685 A | 4/2000 |
| CN | 1251321 A | 4/2000 |
| CN | 1390816 A | 1/2003 |
| CN | 1588690 A | 3/2005 |
| WO | WO 2006/070881 A1 * | 7/2006 |

OTHER PUBLICATIONS

Machine translation of CN 1250685.*
Machine translation of CN 1251321.*
Will et al, "Microwave-assisted heterogeneous gas-phase catalysis," Chem. Eng. Tech. 2004, vol. 27, No. 2, pp. 113-122 (see especially p. 116, Fig. 6).*
International Search Report, dated Feb. 15, 2007, corresponding to PCT/CN2006/003015.
Xu, et al., "Study on Methane Coupling Under Microwave Plasma" Journal of Nanjing Normal University (Natural Science), vol. 27, No. 4, 2004, pp. 55-58.
Cheng, et al., "Study on the Microwave Plasma Temperature in Microwave Chemical Reactor" Chinese Journal of Electron Devices, vol. 28, No. 3, Sep. 2005, pp. 556-558.
Zhang, et al., "A Study on Coupling of Methane to $C_2$ Hydrocarbons Under Microwave Plasma with Low Pressure" Chinese Journal of Electron Devices, vol. 28, No. 3, Sep. 2005, pp. 559-561.

* cited by examiner

RECESS WAVEGUIDE MICROWAVE CHEMICAL PLANT FOR PRODUCTION OF ETHENE FROM NATURAL GAS AND THE PROCESS USING SAID PLANT

CROSS-REFERENCE TO RELATED APPLICATION(S)

This application is a National Phase Patent Application and claims the priority of International Application Number PCT/CN2006/003015, filed on Nov. 10, 2006, which claims priority of Chinese Patent Application Number 200610037890.9, filed on Jan. 20, 2006.

FIELD OF THE INVENTION

The present invention relates to a process for producing ethene from natural gas by using resonant cavity-type recess waveguide microwave chemical plant, which falls into the technical field of microwave technique for producing ethene from natural gas by using resonant cavity-type recess waveguide microwave chemical plant.

BACKGROUND OF THE INVENTION

Ethene is one of the most important basic raw materials in chemical industry, and is also one of the chemical products with the largest output in the world. It is the basic raw material for producing various organic chemical products and synthetic materials.

Presently, the industrial process for producing ethene worldwide mainly comprises cracking light oil or naphtha at high temperature. A large amount of petroleum is consumed every year, and the petroleum resources on the earth keep on shrinking day by day.

The proved global natural gas reserves are about $134 \times 10^{12}$ cubic meters, and the number of recently discovered large natural gas fields keeps on increasing. If natural gas is adopted to replace petroleum for producing ethene, the pressure on petroleum demand can be greatly alleviated, and the development of natural gas chemical industry can be also benefited.

Methane is the major component (more than 90%) of dry natural gas; for purpose of convenience, sometimes methane is mentioned instead of natural gas from this point to the end of the present invention.

In worldwide laboratory studies, two conventional heating methods are adopted for converting methane into ethene, i.e. indirect method, and direct method. The indirect method comprises (1) ethene is generated from methane via methanol, which has the disadvantage of high energy consumption during gas generation; or (2) ethene is generated from methane via synthetic gas, in which the issue of how to inhibit regeneration of methane during reaction process has to be addressed.

The most important method in the direct method is oxidation coupling of methane. In 1982, G. E. Keller and M. M. Bhasin from UCC (US) published the result of ethene production through catalysis oxidation coupling of methane for the first time. Since then, researchers worldwide mainly focus on study in two aspects: (1) searching for high quality catalyst, (2) improving reactor. Y. Jiang, et al. believe that ethene should have single-pass yield above threshold value of 40% to make production of ethene from methane economically feasible. But until today, the ethene single-pass yield is still below 30%.

Therefore, production of ethene from methane through conventional heating method is still in research stage, and a method for achieving industrial production with good economic benefit is still unavailable.

Another method for producing ethene from methane is microwave chemical method, including plasma chemical method. The microwave chemical reaction has two significant advantages: (1) chemical reaction rate is greatly improved; (2) reaction that is hard to carry out from the point of view of conventional thermodynamics can be relatively easy to carry out. Methane is the organic molecule with most stable structure, and the reaction for producing ethene from methane through dehydrogenation coupling in absence of oxygen only can be carried out at high temperature of 1400° C. But with microwave chemical method, the methane can be easily decomposed into ethene. Although according to literature publications worldwide, ethene single-pass yield has already reached 30% which is higher than that of conventional heating method, the yield is still lower than 40% which is the internationally proved threshold value for economic feasibility.

Available microwave chemical experiments are mainly carried out in rectangular waveguide or resonant-cavity formed by the rectangular waveguide, which are still limited in rectangular waveguide; obstacles for producing ethene from methane (natural gas) by microwave chemical method comprises:
(1) Small resonant-cavity volume for microwave chemical reaction;
(2) Small flow rate of feed gas methane (natural gas);
(3) Ethene single-pass yield less than 40%.

Therefore, until today, the technical background is that no matter whether ethene is produced from methane (natural gas) by conventional heating method or microwave chemical method, the three obstacles including small cavity volume, low methane flow rate, and low ethene single-pass yield still need to be addressed. These obstacles, well known worldwide, have been intensively studied by numerous scientists for dozens of years, and are still unsettled.

CONTENTS OF THE INVENTION

Technical difficulty: the object of the present invention is to overcome the disadvantages in the prior arts, provide a resonant cavity-type recess waveguide microwave chemical plant for producing ethene from natural gas, and production process thereof for chemical industrial production, and achieve production of ethene from natural gas with low cost and high efficiency.

Technical Scheme: the resonant cavity-type recess waveguide microwave chemical plant for producing ethene from natural gas in the present invention is formed by a recess waveguide, a mode transducer and coupling orifice plate, an adjustable short-circuiting plunger (or fixed short-circuiting plate), and a chemical reactor; wherein with the recess waveguide as main body, the mode transducer and coupling orifice plate is provided at the left side of the recess waveguide, the adjustable short-circuiting plunger (or fixed short-circuiting plate) is provided at the right side of the recess waveguide, and the chemical reactor is across the recess waveguide.

The said recess waveguide refers to a round recess waveguide, an elliptical recess waveguide, a rectangular recess waveguide, a trapezoid recess waveguide, a V-shaped recess waveguide, or a waveguide with cross section in arbitrary shape. A wedge-shaped high power matched load (dry load or water load) relevant to working wavelength is fitted at the end part of metal parallel flat plates at two wings of the recess waveguide. The microwave working frequency of the recess waveguide is within 0.3-22 GHz. The recess waveguide can be operated in continuous wave or pulsed wave.

The recess waveguide comprises a left metal flat plate, a right metal flat plate, a wedge-shaped matched load, an insulation strip, and a cutoff waveguide. The left metal flat plate and the right metal flat plate are symmetric in shape; the insulation strips are respectively arranged at two sides between the left metal flat plate and the right metal flat plate; the wedge-shaped matched load is arranged at inner side of the insulation strip; a space is formed between the left metal flat plate and the right metal flat plate; a through hole is arranged along the lengthwise direction of the flat plate at the symmetric center of the end faces of the left and right metal flat plate end faces of the recess waveguide.

For the sake of convenience, from this point to the end of the present patent disclosure, the round recess waveguide is adopted as example for describing various recess waveguides.

The mode transducer is used for converting mode of microwave input into the waveguide from the microwave source into required microwave mode satisfying requirement of the recess waveguide. This can be achieved by using one-stage transducer or multi-stage transducers connected in series. The coupling orifice plate is used for coupling the energy of the microwave source into the resonant cavity, which can be disposed at the input end or the output end of the mode transducer, or between the multi-stage transducers. For achieving aforementioned two functions, multiple combination schemes are available; here only one scheme is adopted as example for explanation as follows.

The mode transducer and coupling orifice plate comprises a first transducer, a flange, a second transducer, and a coupling orifice plate. The first transducer is rectangular waveguide to round waveguide transducer. The second transducer comprises an upper insulation strip, a lower insulation strip, an upper wedge-shaped matched load, a lower wedge-shaped matched load, a left metal flat plate, and a right metal flat plate; wherein the shape formed by the upper insulation strip, the lower insulation strip, the upper wedge-shaped matched load, the lower wedge-shaped matched load, the left metal flat plate, and the right metal flat plate is consistent to the recess waveguide. The central through hole connected with the recess waveguide is in shape of frustum. The outer side of the central through hole of the frustum is connected with the first transducer, the outer end of the first transducer is connected with the flange, and the coupling orifice plate is provided on the flange.

The short-circuiting plunger is an important part of the resonant cavity, which has two forms: adjustable short-circuiting plunger or fixed short-circuiting plate. Here the adjustable short-circuiting plunger is adopted as example for description.

The adjustable short-circuiting plunger comprises a first short-circuiting plunger metal plate, a second short-circuiting plunger metal plate, a third short-circuiting plunger metal plate, a first round insulation gasket, a second round insulation gasket, a hollow round tube, a metal round rod, a sleeve, and a metal flat plate; wherein the first short-circuiting plunger metal plate, the second short-circuiting plunger metal plate, the third short-circuiting plunger metal plate, the first round insulation gasket, and the second round insulation gasket are spaced from each other, the center of which is fixed at one end of the hollow round tube; the other end of the hollow round tube is disposed in the sleeve; the sleeve is fixed in the center of the metal flat plate; and the metal round rod is in the middle of the hollow round tube.

The chemical reactor comprises a reactor made from low-loss material, an upper end cover, a lower end cover, a gas inlet tube, a gas outlet tube, an exciter, and a Langmuir probe; wherein the upper end cover, the gas inlet tube, the lower end cover, and the gas outlet tube are respectively at two ends of the chemical reactor; the exciter is located in the middle of the chemical reactor; and the Langmuir probe is arranged in the chemical reactor and fixed on the upper end cover.

The method for producing ethene from natural gas by using the resonant cavity-type recess waveguide microwave chemical plant comprises:

(1) adopting a large-size resonant cavity-type recess waveguide microwave chemical plant with working frequency within 0.3-22 GHz, wherein the microwave source can adopt continuous wave or pulsed wave;
(2) allowing the resonant cavity-type recess waveguide microwave chemical plant to be in resonant state, and allowing the reactor to be in vacuum state;
(3) selecting hydrogen as auxiliary gas;
(4) regulating pressures of feed natural gas and auxiliary hydrogen gas to 1-20 atm, respectively introducing them into the reactor via different flow meters for metering flow rates of the different gases;
(5) adopting feed natural gas and auxiliary hydrogen gas flow rate ratio, i.e. natural gas: hydrogen gas, at 50:1-1:20;
(6) mixing the feed natural gas and the auxiliary hydrogen gas in a gas mixture cabinet, and introducing into quartz reactor of the resonant cavity-type recess waveguide microwave chemical plant via the feed gas inlet tube and the upper end cover;
(7) regulating the total pressure of the mixed gas in the quartz reactor to $1\times10^{-4}$–20 atm, and making the total pressure of the mixed gas in the quartz reactor slightly lower than the pressure of the feed natural gas and the auxiliary hydrogen gas;
(8) switching on the microwave source power supply, regulating microwave output power to several dozen watts to several hundred kilowatts according to auxiliary gas type, flow rate ratio, and gas mixture pressure, and allowing the gas mixture in the quartz reaction tube to discharge so as to generate microwave plasma, wherein discharge condition can be learned from the Langmuir probe and the cutoff waveguide;
(9) then fine tuning microwave output power to obtain required product, wherein the required product ethene in liquid state can be collected in the condensation trap.

Figure 1:
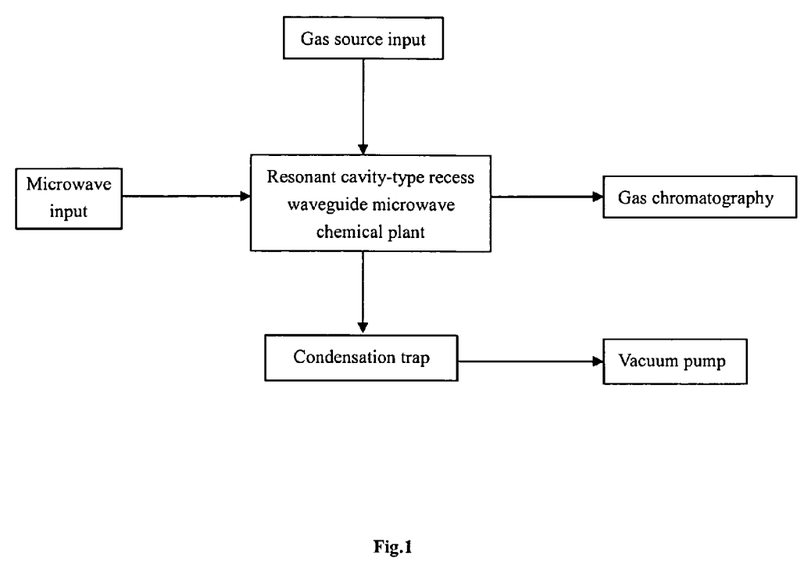
FIG. 1 is the block diagram for production of ethene from natural gas by using the resonant cavity-type recess waveguide microwave chemical plant.

The present invention is designed according to electromagnetic field theory, microwave technology, plasma technology, and chemical engineering principles. The resonant cavity-type recess waveguide microwave chemical plant for the production of ethene from natural gas is shown in FIG. 1. The working principle is that: microwave generated from power source is input into the recess waveguide resonant cavity via a circulator, a directional coupler, and a coupling orifice plate, the reaction tube of the chemical reactor is through the recess waveguide along two wings thereof, and the resonant cavity is allowed to be in resonant state; natural gas flows into the resonant cavity from one end of the reaction tube, free electrons acquire energy under the action of microwave electromagnetic field to inelastically collide with methane molecules and hydrogen molecules to generate more electrons, and newly generated free electrons acquire energy again to collide with methane molecules and hydrogen molecules again to generate more electrons to generate electron avalanche phenomena, wherein free electrons are increased like avalanche until gas breakdown discharges to generate plasma with overall electrical neutrality. The high energy electrons make C—H bond of methane molecule and H—H bond of hydrogen molecule break via inelastic collision to generate numerous free radicals with active chemical properties; product is generated through their various combinations, and composition of the product is shown by gas chromatography. The generated ethene flows out of the resonant cavity along the chemical reaction tube into the condensation trap.

Figure 2:
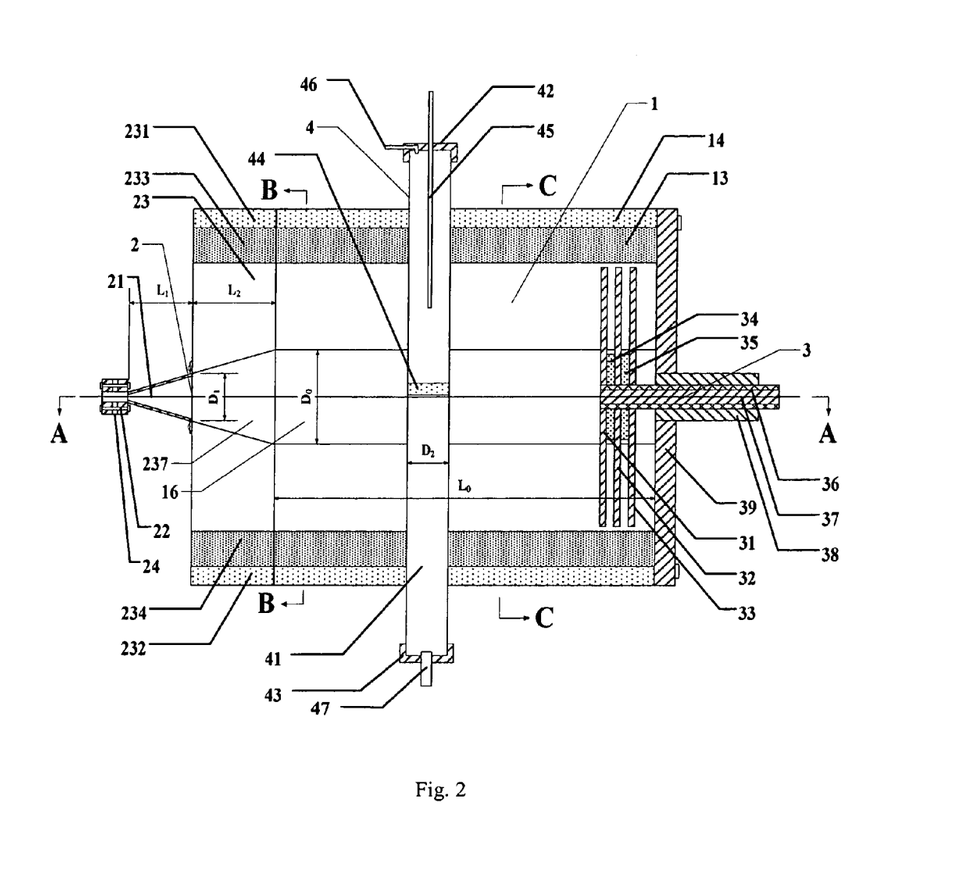
FIG. 2 is the front view and section view of the resonant cavity-type recess waveguide microwave chemical plant.

For the convenience of description, the present invention is described by two parts: (1) the resonant cavity-type recess waveguide microwave chemical plant as shown in FIG. 2; (2) production of ethene from natural gas by using the resonant cavity-type recess waveguide microwave chemical plant. The detailed description is as follows:

1. The Resonant Cavity-Type Recess Waveguide Microwave Chemical Plant (1) Recess Waveguide The said recess waveguide refers to a round recess waveguide, an elliptical recess waveguide, a rectangular recess waveguide, a trapezoid recess waveguide, a V-shaped recess waveguide, or a wave guide with cross section in arbitrary shape. A wedge-shaped high power matched load (dry load or water load) relevant to working wavelength is fitted at the end part of metal parallel flat plates at two wings of the recess waveguide. The microwave working frequency of the recess waveguide is within 0.3-22 GHz, and various allowable civil or industrial frequencies worldwide can be adopted, such as 0.434 GHz, 0.915 GHz, 2.45 GHz, or 5.80 GHz, etc. The recess waveguide can be operated in continuous wave or pulsed wave, which can work at low power or high power. For the convenience of description, the round recess waveguide is adopted as example for detailed explanation.

Figure 3:
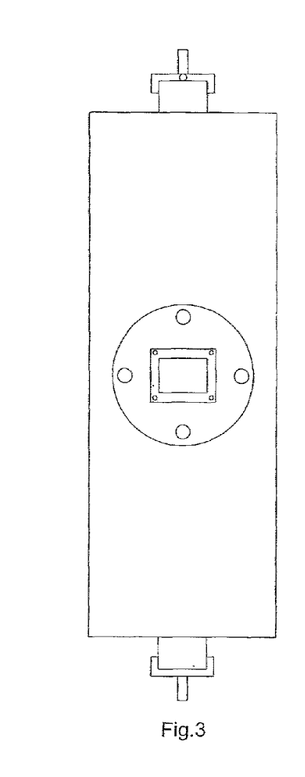
FIG. 3 is the side view of the resonant cavity-type recess waveguide microwave chemical plant.
Figure 4:
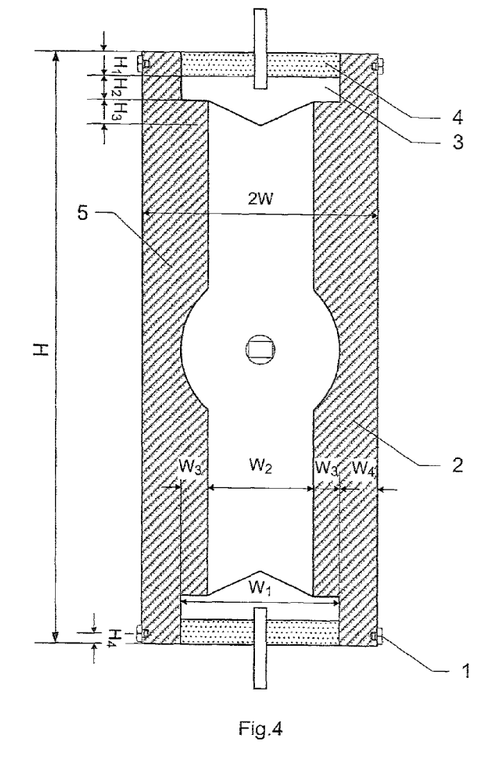
FIG. 4 is the BB section view of the resonant cavity-type recess waveguide microwave chemical plant.
Figure 5:
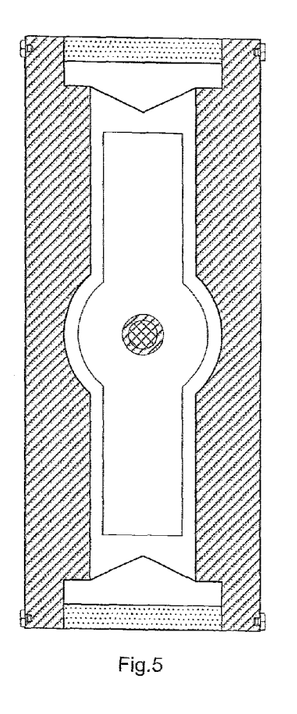
FIG. 5 is the CC section view of the resonant cavity-type recess waveguide microwave chemical plant.
Figure 6:
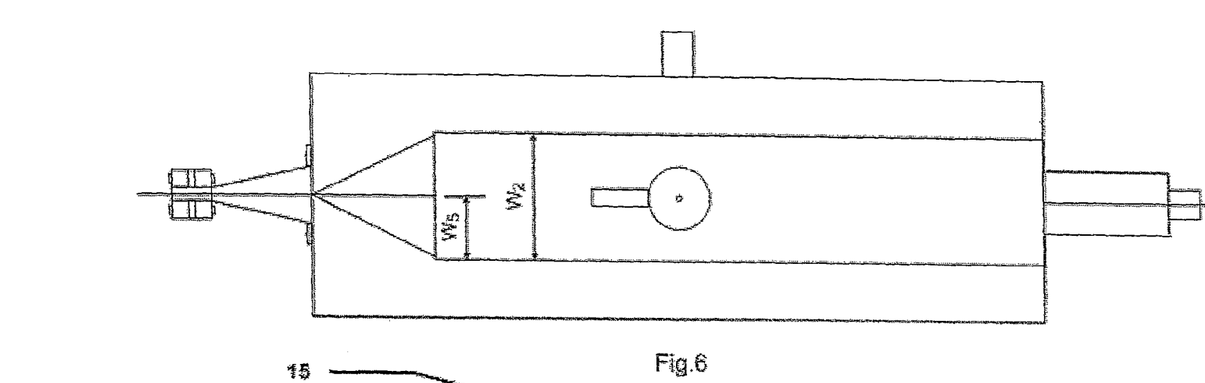
FIG. 6 is the horizontal view of the resonant cavity-type recess waveguide microwave chemical plant.
Figure 7:
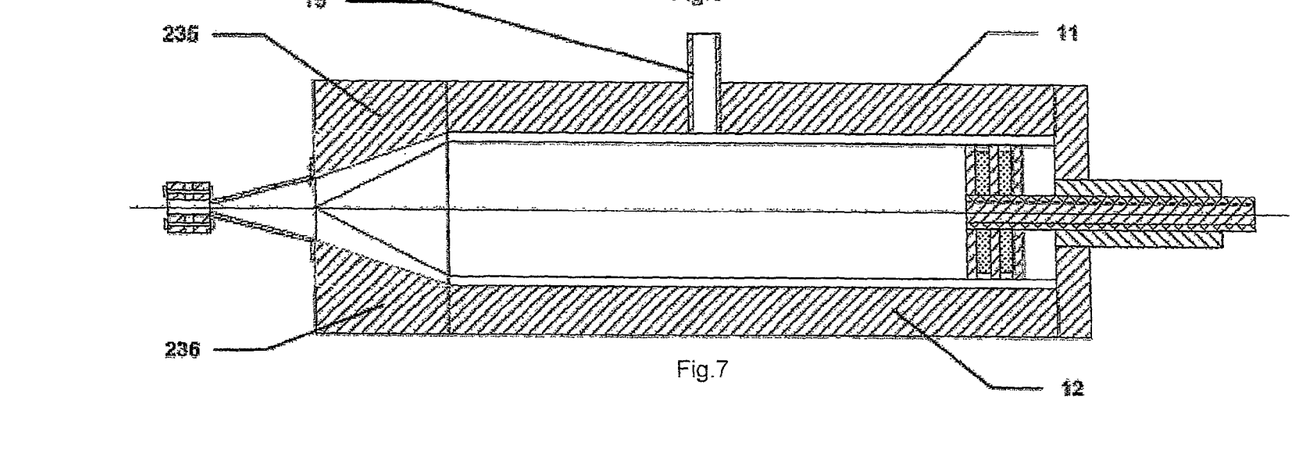
FIG. 7 is the AA section view of the resonant cavity-type recess waveguide microwave chemical plant.
Figure 8A:
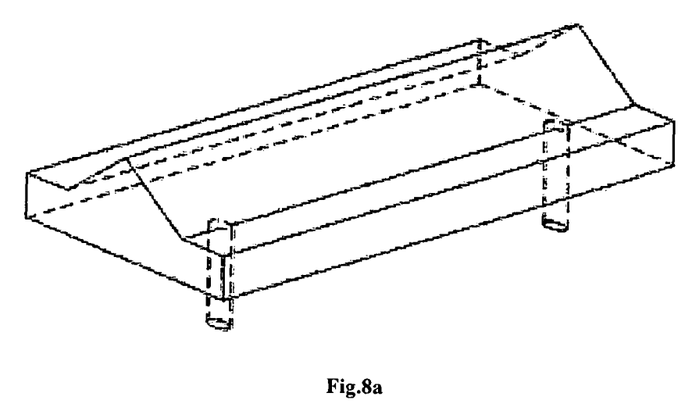
FIG. 8*a* is 3D image of the wedge-shaped matched load.
Figure 8B:
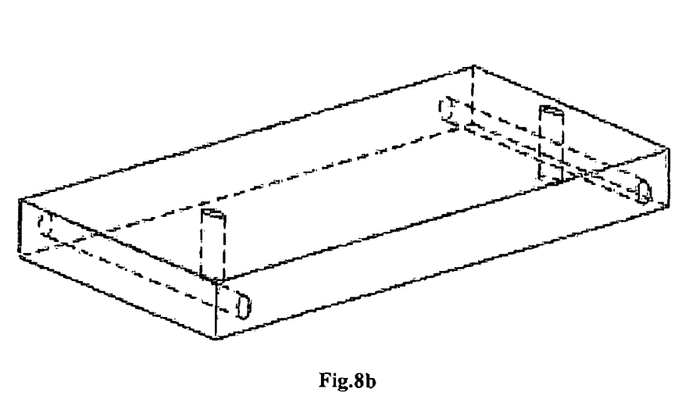
FIG. 8*b* is 3D image of the insulation strip.
Figure 9:
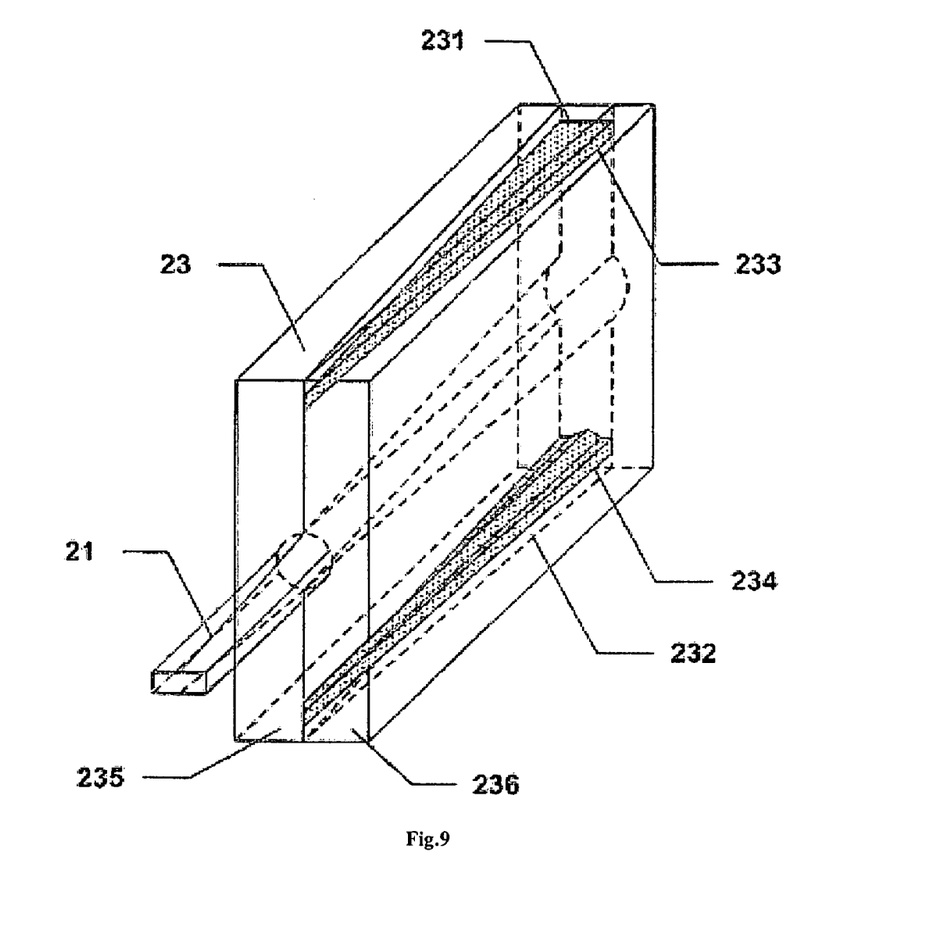
FIG. 9 is the 3D image of the mode transducer.

The round recess waveguide adopts two metal flat plates spaced by upper and lower insulation strips, and wedge-shaped matched loads (dry load or water load) are fitted at inner sides of the insulation strips. The height of the wedge is integral multiple of half of the working wavelength of the electromagnetic wave. A round through hole with diameter of $D_0$ is arranged at the symmetric center of the end faces of the two metal flat plates along the lengthwise direction of the flat plate, as shown in FIG. 2 and BB section view. The axial direction of the round hole is the propagation direction of the electromagnetic wavelength, which is simply called as axial direction. The high frequency recess waveguide wedge-shaped matched load is blow molded into desired shape from quartz glass, and has water inlet and outlet tubes, which is as shown in FIG. 3. The load also can be matched water load of other forms. The recess waveguide insulation strip is made from ceramic material, as shown in FIG. 3. If dry load is adopted, the shape and the size shown in FIG. 3 are also adopted. A plasma spectrum observation hole is opened on the side wall of the recess waveguide through hole. A cutoff waveguide is fitted outside of the hole, and microwave energy leaked from the hole is less than national standard. The hole should ensure that through the hole, light generated by the plasma inside the quartz reaction tube can be observed, and the plasma temperature or spectrum generated by the plasma can be measured.

(2) Mode Transducer and Coupling Orifice Plate:

For achieving two functions, i.e. mode conversion and energy coupling, multiple combination schemes are available. Here, only one scheme is adopted for description. The mode transducer and coupling orifice plate comprises a first transducer, a second transducer, a flange and a coupling orifice plate. The first transducer is rectangular waveguide to round waveguide transducer. The second transducer is round waveguide to round recess waveguide transducer. The first transducer has one end with cross section of rectangular waveguide and the other end with cross section of round waveguide, in which transition there between is linear, i.e. space formed by lineally connecting every point on the rectangular perimeter and corresponding points on the circumference. The second transducer has one end with cross section of the round waveguide and the other end with cross section of the round recess waveguide having a different diameter. Distance of two points of the largest opening of V-shape formed by extending from perpendicular central line of one end of the round cross section in V-shape is equal to distance between the two metal flat plates of the round recess waveguide. A connection hole is provided on the waveguide wall of the round recess waveguide end. A rectangular waveguide flange is fitted on the cross section end of the rectangular waveguide. A coupling orifice plate is arranged on the flange, which can be inductive or capacitive, and in round, rectangular or other shapes. The coupling orifice plate is also connected with input waveguide for coupling the microwave energy into the resonant cavity.

(3) Adjustable Short-Circuiting Plunger:

The short-circuiting plunger is an important part of the resonant cavity, which may have two forms: adjustable short-circuiting plunger or fixed short-circuiting plate. Here the adjustable short-circuiting plunger is adopted as example for description.

The round recess waveguide has one end connected with the mode transducer and coupling orifice plate, and the other end fitted with the adjustable short-circuiting plunger to form the resonant cavity. The adjustable short-circuiting plunger is formed by a metal flat plate with shape identical to that of the hollow pattern of the waveguide end face, which can be made from material same as the waveguide material, and has thickness of ¼ wavelength. A gap is provided between the metal flat plate and the waveguide to space them apart; and the metal flat plate of the short-circuiting plunger can be formed by one or more pieces. An insulation gasket with thickness of ¼ wavelength is adopted to space the metal flat plates. The insulation gaskets have diameters slighter smaller than diameter $D_0$ of the recess waveguide through hole, which are made from ceramic material, and are fixed on a hollow round tube. A metal round rod with diameter same as that of the hollow round tube is disposed in the hollow round tube. The round tube end face, the round rod end face, and the first metal flat plate are in the same plane. The hollow round tube is through a sleeve; the sleeve passes through the hole at the symmetric center of the metal flat plate of the recess waveguide end face, and is fixed thereon. The hollow round tube is connected with a mechanical adjustment mechanism to allow the short-circuiting plunger to parallel move in the recess waveguide.

(4) Chemical Reactor:

The chemical reactor is a place where microwave and reactant substance react, therefore the chemical reactor must be located inside the resonant cavity of the round recess waveguide. The reactor can be made from quartz, ceramics, low-loss glass, or other nonmetallic solid material with low loss in electromagnetic field, which is preferably made from transparent quartz for benefiting observation of spectrum generated by the plasma. The chemical reactor can be in shape of a round tube, or other shapes according to requirement, in which the shape should be helpful for carrying out chemical reaction, be able to be accommodated in the resonant cavity of the recess waveguide, and provided with an inlet tube for feed gas and a gas outlet tube for product.

An exciter is arranged in the chemical reactor, which can be a metallic exciter, a nonmetallic exciter (including semiconductor), or a mixed metallic-nonmetallic exciter. The materials suitable for the metallic exciter comprise tungsten, iron, nickel, or alloy thereof. The material suitable for nonmetallic exciter is graphite. The size and shape of the exciter are relevant to working frequency of microwave source.

A Langmuir probe is arranged in the chemical reactor for measuring parameters of the plasma. The probe can be single, double, or multiple. For example, double Langmuir probe is inserted into the plasma and applied with voltage to measure current passing the probe to give current-voltage characteristic curve, so as to obtain various parameters like the plasma density, or electron temperature from the measurement data.

The probe can be made from metallic material with high temperature resistance, which is usually placed in the flat plate zone of the recess waveguide for avoiding influence on microwave discharge and chemical reaction while measuring plasma parameters.

On the whole, the resonant cavity-type recess waveguide microwave chemical plant is formed by assembling the recess waveguide, the mode transducer and coupling orifice plate, the adjustable short-circuiting plunger (or fixed short-circuiting plate), and the chemical reactor according to FIG. 2.

2. Production of Ethene from Natural Gas by Using Resonant Cavity-Type Recess Waveguide Microwave Chemical Plant
  (1) Adopting a large-size resonant cavity-type recess waveguide microwave chemical plant with working frequency within 0.3-22 GHz, wherein the microwave source can adopt continuous wave or pulsed wave;
  (2) allowing the resonant cavity-type recess waveguide microwave chemical plant to be in resonant state, and allowing the reactor to be in vacuum state;
  (3) selecting appropriate auxiliary gas, wherein the hydrogen gas is used as the auxiliary gas;
  (4) regulating pressures of feed methane (natural gas) and auxiliary hydrogen gas to 1-20 atm, respectively introducing them into the reactor via different flow meters for metering flow rates of the different gases;
  (5) Adopting feed methane (natural gas) and auxiliary hydrogen gas flow rate ratio, i.e. natural gas: hydrogen gas, at 50:1-1:20;
  (6) Mixing the feed methane (natural gas) and the auxiliary hydrogen gas in a gas mixture cabinet, and introducing into quartz reaction tube of the resonant cavity-type recess waveguide microwave chemical plant via the feed gas inlet tube and the upper end cover;
  (7) Regulating the total pressure of the mixed gas in the quartz reaction tube slightly lower than the pressure of the feed methane (natural gas) and the auxiliary hydrogen gas;
  (8) Switching on the microwave source power supply, regulating microwave output power, and allowing the gas mixture in the quartz reactor to discharge so as to generate microwave plasma, wherein discharge condition can be learned from the Langmuir probe and the cutoff waveguide;
  (9) Then regulating microwave output power to obtain required product, wherein the required product ethene in liquid state can be collected in the condensation trap.

The key factors for ensuring high single-pass yield of production of ethene from methane (natural gas) comprise selection of resonant cavity-type recess waveguide microwave chemical plant, power intensity of microwave, gas pressure, variety of gas (for example hydrogen gas) mixed with methane (natural gas), and flow rate ratio of methane (natural gas) and auxiliary hydrogen gas.

The working principle: electrons in the microwave electromagnetic field acquire energy; when the high energy electrons inelastically collide with gas molecules, ionization of methane molecules and hydrogen molecules are induced to generate plasma with overall electric neutrality. The C—H bond of the methane molecule and the H—H bond of the hydrogen molecule are broken through inelastic collision of the high energy electrons to generate free radicals; those free radicals are very active, which can generate new substance like ethene by recombining in certain way. This is the principle of ethene conversion from natural gas (methane), from which it can be learned that it is very important to build an appropriate environment capable of providing strong electromagnetic field energy; the resonant cavity-type recess waveguide microwave chemical plant in the present invention can satisfy the aforementioned requirements.

Benefits of the Invention:

(1) Presently, ethene production adopts petroleum as raw material, due to long term exploitation, the global petroleum resources keep on shrinking day by day. Production of ethene from natural gas in place of petroleum provides a new approach for raw material, which can greatly alleviate pressure on petroleum demand. And the global natural gas resources are relatively abundant.

(2) The present invention can be adopted in region with rich natural gas resources, with the advantage of low investment, quick setup, and low cost, which can promote cost reduction of downstream products using ethene as raw material, and improve competition capability in world market.

(3) The present invention is environment friendly. Production of ethene from natural gas by microwave method involves no harmful substances in feed material, production process, and product. The whole production process is a clean production.

(4) The present invention is beneficial to development of natural gas chemical industry.

(5) Compared with other waveguide structures in the microwave technical field, the recess waveguide has the merit of large-size, and only the present invention is applicable to industrial production of ethene.

(6) The present invention requires no catalyst.

DESCRIPTION OF DRAWINGS

FIG. 8 is the 3D image of the recess waveguide wedge-shaped matched load and the insulation strip, in which

SYMBOL DESCRIPTION 1 recess waveguide
11 left metal flat plate
12 right metal flat plate
13 wedge-shaped matched load
14 insulation strip
15 cutoff waveguide
2 mode transducer and coupling orifice plate
21 first transducer
23 second transducer
231 upper insulation strip of the second mode transducer
232 lower insulation strip of the second mode transducer
233 upper wedge-shaped matched load of the second mode transducer
234 lower wedge-shaped matched load of the second mode transducer
235 left metal flat plate of the second mode transducer
236 right metal flat plate of the second mode transducer
3 adjustable short-circuiting plunger
31 first short-circuiting plunger metal plate
32 second short-circuiting plunger metal plate
33 third short-circuiting plunger metal plate
34 first round insulation gasket
35 second round insulation gasket
36 hollow round tube
37 metal round rod
38 sleeve
39 metal flat plate
4 chemical reactor
41 reactor
42 upper end cover
43 lower end cover
44 exciter
45 Langmuir Probe
47 gas outlet tube
$D_0$ diameter of round recess waveguide through hole
$D_1$ diameter of outer end of frustum through hole
$D_2$ diameter of chemical reactor
$L_0$ length of round recess waveguide
$L_1$ length of first transducer
$L_2$ length of second transducer
H total height of recess waveguide
$H_1$ height of recess waveguide insulation strip
$H_2$ height of base of recess waveguide wedge-shaped matched load
$H_3$ wedge height
$W_1$ width of recess waveguide wedge-shaped matched load
$W_2$ distance between parallel flat plates of the recess waveguide

EMBODIMENT OF THE INVENTION

For the convenience of description, the present invention is described in two parts: (1) the first part comprises implementation of the resonant cavity-type recess waveguide microwave chemical plant; (2) the second part comprises implementation of production of ethene from natural gas by using the resonant cavity-type recess waveguide microwave chemical plant. The detailed description is as follows:

1) Implementation of the Resonant Cavity-Type Recess Waveguide Microwave Chemical Plant the resonant cavity-type recess waveguide microwave chemical plant is formed by a recess waveguide 1, a mode transducer and coupling orifice plate 2, an adjustable short-circuiting plunger 3, and a chemical reactor 4; wherein with the recess waveguide 1 as main body, the mode transducer and coupling orifice plate 2 is provided at the left side of the recess waveguide 1, the adjustable short-circuiting plunger 3 is provided at the right side of the recess waveguide 1, and the chemical reactor 4 is across the recess waveguide 1.

The recess waveguide 1 comprises a left metal flat plate 11, a right metal flat plate 12, a wedge-shaped matched load 13, an insulation strip 14, and a cutoff waveguide 15. The left metal flat plate 11 and the right metal flat plate 12 are symmetric in shape; the insulation strips 14 are respectively arranged at two sides between the left metal flat plate 11 and the right metal flat plate 12; the wedge-shaped matched load 13 is arranged at inner side of the insulation strip; a space is formed between the left metal flat plate and the right metal flat plate; a through hole is arranged along the lengthwise direction of the flat plate at the symmetric center of the left and right metal flat plate end faces of the recess waveguide 1.

The mode transducer and coupling orifice plate 2 comprises a first transducer 21 and a second transducer 23. The first transducer 21 is rectangular waveguide to round waveguide transducer. The second transducer 23 comprises an upper insulation strip 231, a lower insulation strip 232, an upper wedge-shaped matched load 233, a lower wedge-shaped matched load 234, a left metal flat plate 235, and a right metal flat plate 236; wherein the shape formed by the upper insulation strip 231, the lower insulation strip 232, the upper wedge-shaped matched load 233, the lower wedge-shaped matched load 234, the left metal flat plate 235, and the right metal flat plate 236 is consistent to the recess waveguide. The central through hole connected with the recess waveguide 1 is in shape of frustum. The outer side of the central through hole of the frustum is connected with the first transducer 21.

The adjustable short-circuiting plunger 3 comprises a first short-circuiting plunger metal plate 31, a second short-circuiting plunger metal plate 32, a third short-circuiting plunger metal plate 33, a first round insulation gasket 34, a round insulation gasket 35, a hollow round tube 36, a metal round rod 37, a sleeve 38, and a metal flat plate 39; wherein the first short-circuiting plunger metal plate 31, the second short-circuiting plunger metal plate 32, the third short-circuiting plunger metal plate 33, the first round insulation gasket 34, and the second round insulation gasket 35 are spaced from each other, the center of which is fixed at one end of the hollow round tube 36; the other end of the hollow round tube 36 is disposed in the sleeve 38; the sleeve 38 is fixed in the center of the metal flat plate 39; and the metal round rod 37 is in the middle of the hollow round tube 36.

The chemical reactor 4 comprises a reactor 41 made from low-loss material, an upper end cover 42, a lower end cover 43, an exciter 44, a Langmuir probe 45, a gas inlet tube 46 and a gas outlet tube 47; wherein the upper end cover 42, the gas inlet tube 46, the lower end cover 43, and the gas outlet tube 47 are respectively at two ends of the chemical reactor 41; the exciter 44 is located in the middle of the chemical reactor 41; and the Langmuir probe 45 is arranged in the chemical reactor 41 and fixed on the upper end cover 42.

(1) Recess Waveguide

Here, round recess waveguide is adopted as example. There are several manufacturing schemes, such as machining, or compression forming by using sheet presser. For the convenience of description, following method is adopted for explanation. The invention can be implemented by scheme as shown in FIG. 2: BB; the manufacture of recess waveguide 1 is as follows: two metal flat plates made of good conductor like copper, brass, or aluminum alloy are provided and machined into same sizes; wherein the length of the flat plate is determined according to practical requirement, as long as the process can achieve; the height H and width W of the flat plate is related to working wavelength $\lambda$; H=10$\lambda$–30$\lambda$, and W=0.35$\lambda$–1.26$\lambda$; edges of both sides of the metal flat plate are fixed by screws; slots, with height of ($H_1+H_2$)=0.15$\lambda$–1.5$\lambda$) and width of $W_1=W_2+2\ W_3$=0.5$\lambda$–2.313$\lambda$, are each milled respectively on the upper and lower end faces along lengthwise direction by using contact boundary line of two flat plates as central line, the length of the slot is same as the length $L_0$ of the round recess waveguide, in which $H_1=0.1\lambda-1\lambda$, $H_2=(½)H_1$, $W_2=0.4\lambda-1.313\lambda$, and $W_3=0.05\lambda-0.5\lambda$; a through hole is bored at the symmetric center of the end face along lengthwise direction, and has diameter of $D_0=0.62\lambda-2.02\lambda$; the screws are dismounted, each metal flat plate has one side with the slot milled off by width of $W_5=(½)W_2$. The processed two metal flat plates are the left metal flat plate 11 and the right metal flat plate 12 of the recess waveguide as shown in FIG. 2:BB.

The wedge-shaped matched load 13 of the recess waveguide 1 is the key part for absorbing electromagnetic wave reaching edges of the metal flat plate to reduce microwave leakage. The height of the wedge is integral multiple of half of the working wavelength of the electromagnetic wave, $H_3=0.5\lambda-3\lambda$. The whole wedge-shaped matched load is fitted at inner side of the insulation strip 14. The upper and lower insulation strips are used for spacing the left metal flat plate 11 and the right metal flat plate 12 of the recess waveguide, which have length same as that of the round recess waveguide, and can be made of insulation material like ceramics. Holes are provided on the insulation strip for passing the gas inlet and gas outlet of the chemical reactor, and the water inlet and water outlet of the wedge-shaped matched load. When power is low, wedge-shaped matched dry load can be used, which has size and shape identical to those of the water load, and made from material (graphite) capable of absorbing microwave strongly.

In FIG. 2, $H_4=0.05\lambda-0.5\lambda$, and $W_4=0.45\lambda-1.364\lambda$.

A plasma spectrum observation hole is opened on the side wall of the through hole of the recess waveguide 1, and the diameter of the hole is within $0.05\lambda-0.1\lambda$. A cutoff waveguide 15 with attenuation value within 100-200 db is fitted outside of the hole, as shown in FIG. 2 AA. The microwave energy leaked from the hole is lower than the national standard. The hole should ensure that through the hole, light generated by the plasma inside the quartz reaction tube can be observed, and the plasma temperature or spectrum generated by the plasma can be measured.

(2) Mode Transducer and Coupling Orifice Plate

The mode transducer and coupling orifice plate 2 is shown in FIG. 2, which is implemented by two parts: the manufacture of the first transducer 21 comprises preparing a wax mold, which has size of rectangular waveguide end correspondingly selected according to working frequency of the microwave source, and diameter of the round waveguide end of $D_1=0.6\lambda-0.9\lambda$; connecting corresponding points at two end faces with straight lines, preparing into copper waveguide by electrocasting technique, melting off the wax mold, surface polishing, fitting flange 22 on the rectangular waveguide end, boring on base of the round waveguide end, and fixing with the second transducer via screws, wherein the total length of the first transducer is $L_1=1\lambda-3\lambda$; the manufacture of the second transducer 23 comprises adopting two metal flat plates (copper, brass or aluminum alloy) with length $L_2=1\lambda-3\lambda$, total width of the two plates $2W=0.35\lambda-1.26\lambda$, and height $H=10\lambda-30\zeta$; fixing edges of the two metal flat plates via screws, machining a frustum through hole at the symmetric center of the end face which has diameter $D_1=0.6\lambda-0.9\lambda$ at one end, and diameter $D_0=0.62\lambda-2.02\lambda$ same as that of the round recess waveguide through hole at the other end, wherein $\lambda$ is wavelength, removing the screw to disassemble into two pieces; machining off a wedge-shape on one side with slot of each metal flat plate, wherein the height of the wedge is equal to length $L_2$ of the metal flat plate, the bottom of the wedge is in shape of a rectangle with longer edge equal to height H of the metal flat plate and the shorter edge equal to $W_5=(½)W_2=0.2\lambda-0.656\lambda$, and the machined surface should be smooth; machining two small ceramic wedges as the upper insulation strip 231 and the lower insulation strip 232 of the second transducer by using ceramic insulation material, wherein the height of the ceramic wedge is also equal to length $L_2$ of the metal flat plate, the bottom of the ceramic wedge is also in shape of rectangle with longer edge $W_2=2W_5$ and shorter edge $H_1=0.1\lambda-1\lambda$; respectively fitting upper/lower wedge-shaped matched load 233 and 234 of the second transducer on inner side of the upper/lower insulation strip 231 and 232 of the second transducer, which can be water load or dry load similar to the wedge-shaped matched load in the recess waveguide, wherein the wedge height is $H_3$; disposing upper and lower ceramic insulation strips together with matched loads between machined left metal plate 235 and right metal plate 236 of the second transducer; fixing with screws; and connecting the mode transducer 2 with the round recess waveguide 1.

The shape of the coupling orifice plate 24 has size same as the flange of the selected standard rectangular waveguide, with thickness of $0.005\lambda-0.1\lambda$. If round hole is opened at its symmetric center, then the hole diameter is smaller or equal to height of the rectangular waveguide; if rectangular coupling hole is opened at its symmetric center, then the rectangular hole has width smaller or equal to width of the rectangular waveguide, and height smaller or equal to height of the rectangular waveguide. If the coupling orifice plate is provided with a narrow slit in direction parallel to its widthwise direction, then capacitive diaphragm is formed; if the coupling orifice plate is provided with a narrow slit in direction parallel to its height direction, then inductive diaphragm is formed. The coupling orifice can be in round, rectangular or other shapes. The size of the slit and orifice can be optimized through measurement.

(3) Adjustable Short-Circuiting Plunger

The adjustable short-circuiting plunger 3 is formed by a metal plate with shape identical to that of the hollow pattern of the end face of the recess waveguide 1, i.e. a first short-circuiting plunger metal plate 31, a second short-circuiting plunger metal plate 32, and a third short-circuiting plunger metal plate 33, and the material adopted can be copper, brass, or aluminum alloy. The thickness of the short-circuiting metal plate is ¼ wavelength. A through hole is provided at the center of the short-circuiting plunger metal plate to allow the plunger to be fitted on a hollow round tube 36. A gap is provided to space the metal flat plate and the waveguide. A first round insulation gasket 34 and a second round insulation gasket 35 with thickness of ¼λ are arranged between the short-circuiting plunger metal plates to space them apart. The gasket diameter is 0.8 times of the diameter $D_0$ of the through hole of the recess waveguide. The first short-circuiting plunger metal plate 31, the first round insulation gasket 34, the second short-circuiting plunger metal plate 32, the second round insulation gasket 35, and the third short-circuiting plunger metal plate 33 are sequentially fitted on the hollow round tube 36 to make the short-circuiting metal plate and the outer diameter of the hollow round tube 36 tightly fitted, so as to prevent arbitrary movement of the short-circuiting plunger metal plate. A metal round rod 37 is disposed in the hollow round tube 36, and the diameter of the rod is same as that of the hollow round tube. The round tube end face, the round rod end face, and the first short-circuiting plunger metal plate 31 are allowed to be in the same plane.

A metal flat plate 39 is fitted on the end face of the recess waveguide 1. A hole is opened at the symmetric center of the plate, a sleeve 38 passes through the hole and is fixed with the metal flat plate 39. The hollow round tube 36 of the short-circuiting plunger assembly passes through the sleeve 38 and is in slide fitting state. The hollow round tube 36 is connected with mechanical regulation mechanism to make the short-circuiting plunger 3 move in parallel in the recess waveguide 1.

(4) Chemical reactor

The reactor 41 is made from low-loss material, such as quartz, high quality ceramics or nonmetallic material which does not absorb microwave. The reactor 41 made from the low-loss material can be in round tube shape or arbitrary shape which can be accommodated by the resonant cavity. Here an example will be given for describing implementation of the chemical reactor.

The reactor 41 made from low-loss material is designed into a round tube shape, and is made of quartz. The reactor has diameter $D_2$ smaller than the distance $W_2$ between parallel flat plates of the recess waveguide 1, as shown in FIG. 2: BB. The height of the reactor is slightly higher than total height H of the recess waveguide 1. The reactor 41 has one end fitted with a vacuum-proof upper end cover 42, wherein the upper end cover 42 is also connected with a feed gas inlet tube 46; the other end of the reactor 41 is fitted with a vacuum-proof lower end cover 43, wherein the lower end cover is connected with a product gas outlet tube 47, and further sequentially connected with a condensation trap and a vacuum pump.

An exciter 44 is disposed inside the quartz round tube reactor 41. The exciter can be made from iron, tungsten or other high temperature resistant metal, or nonmetallic material like graphite. The exciter can be in arbitrary shape beneficial for gas discharge. Langmuir Probe 45 is disposed in the reactor 41 made of low-loss material, located at position $1\lambda$-$3\lambda$ above the central round through hole of the recess waveguide, and fixed on the upper end cover 42.

Now the aforementioned parts are assembled according to FIGS. 2 and 1 to form the resonant cavity-type recess waveguide microwave chemical plant. The assembly comprises:

(1) removing machine oil on each parts, and cleaning;
(2) assembling each parts of the short-circuiting plunger 3 including the first short-circuiting plunger metal plate 31, the second short-circuiting plunger metal plate 32, the third short-circuiting plunger metal plate 33, the first round insulation gasket 34, the second round insulation gasket 35, the hollow round tube 36, and the metal round rod 37 according to FIG. 2 into an assembly;
(3) arranging the left metal flat plate 11, the right metal flat plate 12, the wedge-shaped matched load 13, the insulation strips 14, and the short-circuiting plunger 4 of the recess waveguide 1 according to FIG. 2, fixing with screw, and reserving corresponding holes on the insulation strips for passing the round tubular chemical reactor;
(4) connecting the first mode transducer 21 and the second mode transducer 23, connecting the other end of the second mode transducer 23 with the recess waveguide, fixing the other end of the first mode transducer 21 with the rectangular waveguide flange 22, and connecting the other end of the rectangular waveguide flange 22 with the coupling diaphragm 24;
(5) fixing the metal flat plate 39 with the sleeve 38 on the other end of the recess waveguide 1 via screws, making the hollow round tube 36 of the short-circuiting plunger 3 pass the sleeve 38 on the metal flat plate 39 and connect with the mechanical adjustment mechanism, and making the short-circuiting plunger 3 movable in the recess waveguide 1 in parallel without any obstacle;
(6) disposing the exciter 44 into the reactor 41;
(7) according to FIG. 2, allowing the reactor 41 to pass one wing of the recess waveguide 1 and extend out of the recess waveguide from the other wing of the recess waveguide 1, fitting the vacuum-proof upper end cover 42 on one end of the reactor 41, and connecting the feed gas inlet tube 46 with the upper end cover 42; fitting the vacuum-proof lower end cover 43 on the other end of the reactor 41, and connecting the lower end cover with the product gas outlet tube 47;
(8) according to FIG. 1, connecting the feed gas inlet tube 46 on the upper end cover 42 with the natural gas pipeline (or methane cylinder) via a flow meter, and connecting the product gas outlet tube 47 on the lower end cover 43 with the vacuum pump via the condensation trap;
(9) according to FIG. 2, inserting Langmuir Probe 45 via hole reserved on the upper end cover 42 to desirable position, and fixing on the upper end cover 42 while making connection airtight;
(10) according to FIG. 2, connecting the cutoff waveguide 15 on outer side of the observation hole of the left metal flat plate 11 of the recess waveguide;
(11) connecting the microwave source with the coupling diaphragm 24 via the circulator and directional coupler, connecting power indicators on two auxiliary arms of the directional coupler, and regulating the short-circuiting plunger to make the resonant cavity in resonant state;

Now, the resonant cavity-type recess waveguide microwave chemical plant for production of ethene from natural gas is completely assembled, and is ready for use.

Implementation of Production of Ethene from Natural Gas by Using Resonant Cavity-Type Recess Waveguide Microwave Chemical Plant Comprises:

(1) adopting a large-size resonant cavity-type recess waveguide microwave chemical plant, which is essential for achieving high single-pass ethene yield of ethene production from natural gas; wherein its working frequency is within 0.3-22 GHz, and the microwave source can adopt continuous wave or pulsed wave;
(2) allowing the resonant cavity-type recess waveguide microwave chemical plant to be in resonant state, and allowing the reactor 41 to be in vacuum state;
(3) selecting appropriate auxiliary gas, wherein hydrogen gas is selected as auxiliary gas;
(4) regulating pressures of feed methane (natural gas) and auxiliary hydrogen gas to 1-20 atm, respectively introducing them into the reactor via different flow meters for metering flow rates of the different gases;
(5) adopting feed methane (natural gas) and auxiliary hydrogen gas flow rate ratio, i.e. methane/hydrogen gas, at 50:1-1:20;
(6) mixing the feed methane (natural gas) and the auxiliary hydrogen gas in a gas mixture cabinet, and introducing into quartz reaction tube of the resonant cavity-type recess waveguide microwave chemical plant via the feed gas inlet tube 46 and the upper end cover 42;
(7) regulating the total pressure of the mixed gas in the quartz reaction tube to $1\times10^{-4}$-20 atm, and making the total pressure of the mixed gas in the quartz reaction tube slightly lower than the pressure of the feed methane (natural gas) and the auxiliary hydrogen gas;
(8) switching on the microwave source power supply, regulating microwave output power to several dozen watts to several hundred kilowatts according to auxiliary gas type, flow rate ratio, and gas mixture pressure, and allowing the gas mixture in the quartz reaction tube to discharge so as to generate microwave plasma, wherein discharge condition can be learned from the Langmuir probe and the cutoff waveguide;

(9) then fine tuning microwave output power to obtain required product, wherein the required product ethene in liquid state can be collected in the condensation trap.

The key factors for ensuring high single-pass yield of ethene production from methane (natural gas) comprise selection of regulated resonant cavity-type recess waveguide microwave chemical plant, power intensity of microwave, gas pressure, variety of gas (for example hydrogen) mixed with methane (natural gas), and flow rate ratio of methane (natural gas) and auxiliary hydrogen gas.

Two examples are as follows, even under same working pressure, different products will be obtained under different input power (continuous wave) and different methane/hydrogen ratio, which proves that parameter changes have significant influence on product.

Example 1

Production of Ethene from Methane

Methane: hydrogen=23 L/min: 1.5 L/min
Working pressure=1 atm
Input power=4.2 KW (continuous wave)
Reaction result
Methane single-pass conversion rate: 99.58%
Ethene single-pass yield: 98.53%
Ethene single-pass selectivity: 98.945%

Example 2

Production of Ethane from Methane

Methane: hydrogen=23 L/min: 0.7 L/min
Working pressure=1 atm
Input power=4.0 KW (continuous wave)
Reaction result
Methane single-pass conversion rate: 96.5%
Ethane single-pass yield: 96.4%
Ethane single-pass selectivity: 99.9%

CONCLUSION ethene and/or ethane can be obtained by using the inventive resonant cavity-type recess waveguide microwave chemical plant under different working parameters, such as input power, methane/hydrogen ratio, and working pressure, etc.

The invention claimed is:

1. A resonant cavity-type recess waveguide microwave chemical plant for production of ethene from natural gas, the chemical plant comprising:
    a recess waveguide;
    a mode transducer and coupling orifice plate;
    an adjustable short-circuiting plunger comprising a sleeve, a hollow round tube in the sleeve, and a metal round rod in the hollow round tube; and
    a chemical reactor;
    wherein the recess waveguide comprises a main body, the mode transducer and coupling orifice plate is at a left side of the recess waveguide, the adjustable short-circuiting plunger is at a right side of the recess waveguide, and the chemical reactor is positioned across the recess waveguide.

2. The resonant cavity-type recess waveguide microwave chemical plant for production of ethene from natural gas as claimed in claim 1, wherein the recess waveguide is a round recess waveguide, an elliptical recess waveguide, a rectangular recess waveguide, a trapezoid recess waveguide, or a V-shaped recess waveguide; a microwave working frequency of the recess waveguide is within from about 0.3 to about 22GHz; and the recess waveguide can be operated in a continuous wave or a pulsed wave mode.

3. The resonant cavity-type recess waveguide microwave chemical plant for production of ethene from natural gas as claimed in claim 2, wherein the recess waveguide comprises:
    a left metal flat plate;
    a right metal flat plate;
    wedge-shaped matched loads;
    insulation strips; and
    a cutoff waveguide;
    wherein the left metal flat plate and the right metal flat plate are symmetric in shape; the insulation strips are respectively arranged at two ends between the left metal flat plate and the right metal flat plate; the wedge-shaped matched loads are respectively arranged at inner sides of the insulation strips; a space is between the wedge-shaped matched loads; and a through hole is arranged along a lengthwise direction of the left and right metal flat plates at a symmetric center of end faces of the left and right metal flat plates.

4. The resonant cavity-type recess waveguide microwave chemical plant for production of ethene from natural gas as claimed in claim 3, wherein the wedge-shaped matched loads comprise dry loads or water loads.

5. The resonant cavity-type recess waveguide microwave chemical plant for production of ethene from natural gas as claimed in claim 1, wherein the recess waveguide comprises:
    a left metal flat plate;
    a right metal flat plate;
    wedge-shaped matched loads;
    insulation strips; and
    a cutoff waveguide;
    wherein the left metal flat plate and the right metal flat plate are symmetric in shape; the insulation strips are respectively arranged at two ends between the left metal flat plate and the right metal flat plate; the wedge-shaped matched loads are respectively arranged at inner sides of the insulation strips; a space is between the wedge-shaped matched loads; and a through hole is arranged along a lengthwise direction of the left and right metal flat plates at a symmetric center of end faces of the left and right metal flat plates.

6. The resonant cavity-type recess waveguide microwave chemical plant for production of ethene from natural gas as claimed in claim 5, wherein the wedge-shaped matched loads comprise dry loads or water loads.

7. The resonant cavity-type recess waveguide microwave chemical plant for production of ethene from natural gas as claimed in claim 1, wherein the mode transducer and coupling orifice plate comprises:
    a first transducer and a second transducer; wherein the first transducer is a rectangular waveguide to round waveguide transducer, and the second transducer comprises:
        an upper insulation strip;
        a lower insulation strip;
        an upper wedge-shaped matched load;
        a lower wedge-shaped matched load;
        a left metal flat plate; and
        a right metal flat plate;
    wherein a shape formed by the upper insulation strip, the lower insulation strip, the upper wedge-shaped matched load, the lower wedge-shaped matched load, the left metal flat plate, and the right metal flat plate corresponds to the recess waveguide; a central through hole connected with the recess waveguide is in a shape of a frustum; and an outer side of the central through hole is connected with the first transducer.

8. The resonant cavity-type recess waveguide microwave chemical plant for production of ethene from natural gas as claimed in claim 1, wherein the adjustable short-circuiting plunger further comprises:
   a first short-circuiting plunger metal plate;
   a second short-circuiting plunger metal plate;
   a third short-circuiting plunger metal plate;
   a first round insulation gasket;
   a second round insulation gasket; and
   a metal flat plate;
   wherein the first short-circuiting plunger metal plate, the second short-circuiting plunger metal plate, the third short-circuiting plunger metal plate, the first round insulation gasket, and the second round insulation gasket are spaced from each other, respective centers of which are fixed at one end of the hollow round tube; and wherein an opposite end of the hollow round tube is disposed in the sleeve; the sleeve is fixed in a center of the metal flat plate; and the metal round rod is in a middle of the hollow round tube.

9. The resonant cavity-type recess waveguide microwave chemical plant for production of ethene from natural gas as claimed in claim 8, wherein the adjustable short-circuiting plunger comprises a short-circuiting plate with a fixed position.

10. The resonant cavity-type recess waveguide microwave chemical plant for production of ethene from natural gas as claimed in claim 1, wherein the chemical reactor comprises:
    a reactor made from low-loss material;
    an upper end cover;
    a lower end cover;
    an exciter;
    a Langmuir probe;
    a gas inlet tube; and
    a gas outlet tube;
    wherein the upper end cover and the gas inlet tube are at one end of the chemical reactor and the lower end cover and the gas outlet tube are at an opposite end of the chemical reactor; the exciter is located in a middle of the chemical reactor; and the Langmuir probe is arranged in the chemical reactor and fixed at the upper end cover.

11. A resonant cavity-type recess waveguide microwave chemical plant for production of ethene from natural gas, the chemical plant comprising:
    a recess waveguide, the recess waveguide being a round recess waveguide, an elliptical recess waveguide, a trapezoid recess waveguide, or a V-shaped recess waveguide;
    a mode transducer and coupling orifice plate;
    an adjustable short-circuiting plunger comprising a sleeve, a hollow round tube in the sleeve, and a metal round rod in the hollow round tube; and
    a chemical reactor;
    wherein the recess waveguide comprises a main body, the mode transducer and coupling orifice plate is at a left side of the recess waveguide, the adjustable short-circuiting plunger is at a right side of the recess waveguide, and the chemical reactor is positioned across the recess waveguide.

\* \* \* \* \*